(12) United States Patent
Jung et al.

(10) Patent No.: US 12,364,152 B2
(45) Date of Patent: Jul. 15, 2025

(54) METHOD FOR MANUFACTURING CONDUCTIVE POLYMER ELECTRODE BY USING DROP CASTING

(71) Applicant: OSONG MEDICAL INNOVATION FOUNDATION, Cheongju-si (KR)

(72) Inventors: Ha Chul Jung, Cheongju-si (KR); Da Hye Kwon, Bucheon-si (KR); Jin Hee Moon, Sejong-si (KR); Young Jin Kim, Cheongju-si (KR); Jin Woo Ahn, Cheongju-si (KR); Won Jung Choi, Cheongju-si (KR); Seung A Lee, Seoul (KR); A Hee Kim, Cheongju-si (KR); Ha Na Park, Cheongju-si (KR)

(73) Assignee: OSONG MEDICAL INNOVATION FOUNDATION, Cheongju-si (KR)

( * ) Notice: Subject to any disclaimer, the term of this patent is extended or adjusted under 35 U.S.C. 154(b) by 672 days.

(21) Appl. No.: 17/437,340

(22) PCT Filed: Apr. 3, 2019

(86) PCT No.: PCT/KR2019/003933
§ 371 (c)(1),
(2) Date: Sep. 8, 2021

(87) PCT Pub. No.: WO2020/204226
PCT Pub. Date: Oct. 8, 2020

(65) Prior Publication Data
US 2022/0149284 A1    May 12, 2022

(51) Int. Cl.
*H10K 71/60* (2023.01)
*C09J 9/02* (2006.01)
*H10K 10/84* (2023.01)

(52) U.S. Cl.
CPC .............. *H10K 71/611* (2023.02); *C09J 9/02* (2013.01); *H10K 71/60* (2023.02);
(Continued)

(58) Field of Classification Search
None
See application file for complete search history.

(56) References Cited

U.S. PATENT DOCUMENTS 10,792,489 B2 * 10/2020 Hatakeyama .......... A61B 5/296
2015/0231610 A1 * 8/2015 Sakurai .............. B01D 53/8628
502/344

FOREIGN PATENT DOCUMENTS

JP          2013-122015 A     6/2013
KR          10-0745193 B1     7/2007
(Continued)

OTHER PUBLICATIONS

CN-102365765-A, Feb. 29, 2012, machine translation (Year: 2012).*
Extended European search report issued on Sep. 9, 2022.
International search report issued on Jan. 3, 2021.

*Primary Examiner* — Barbara J Musser
(74) *Attorney, Agent, or Firm* — LEEPI

(57) ABSTRACT

In a method for manufacturing conductive polymer electrode by using drop casting, a conductive material is dispersed in a solution, to form a first mixing solution. A first polymer is added and dispersed to the first mixing solution, to form a second mixing solution. A second polymer solution is added and dispersed to the second mixing solution, to form a third mixing solution. The third mixing solution is dropped on a hot plate using a pipette and a solution of the third mixing solution is evaporated, to form a conductive polymer. The adhesive patch is formed. The adhesive patch is attached to the conductive polymer.

2 Claims, 5 Drawing Sheets

(52) U.S. Cl.
CPC ...... *C09J 2203/326* (2013.01); *C09J 2301/41* (2020.08); *H10K 10/84* (2023.02)

(56) References Cited

FOREIGN PATENT DOCUMENTS

| | | |
|---|---|---|
| KR | 10-2008-0040632 A | 5/2008 |
| KR | 10-2008-0090513 A | 10/2008 |
| KR | 10-1139927 B1 | 5/2010 |
| KR | 10-2012-0090594 A | 8/2012 |
| KR | 10-2016-0049555 A | 5/2016 |
| KR | 10-2016-0107879 A | 9/2016 |
| KR | 10-1719143 B1 | 3/2017 |
| KR | 2018-0096248 A | 8/2018 |
| KR | 10-2019-0066223 A | 6/2019 |

\* cited by examiner

METHOD FOR MANUFACTURING CONDUCTIVE POLYMER ELECTRODE BY USING DROP CASTING

BACKGROUND

1. Field of Disclosure

The present disclosure of invention relates to a method for manufacturing conductive polymer electrode by using drop casting, and more specifically the present invention relates to a method for manufacturing a conductive polymer electrode using a carbon nanofiber and polymer materials via the drop casting.

2. Description of Related Technology

In a metal electrode used for a conventional thin-film transistor, a contact interface layer with an organic semiconductor is unstable so that characteristics of a device may be decreased. Thus, to solve the above problem, a study on replacing the conventional metal electrode by an organic electrode has been developed.

For example, the organic electrodes, such as a conductive polymer like PEDOT/PSS, polyaniline (PANI) polypyrrole (PPy), and so on, carbon nanotube and graphene, have been studied.

Korean laid-open patent No. 10-2012-0090594 discloses the technology of drying the conductive polymer aqueous solution to form a polymer electrode, and Korean laid-open patent No. 10-2016-0049555 discloses a light-emitting diode in which graphene oxide is used for the electrode.

However, in the conventional organic electrode, the conductivity decreases as resistance of the organic electrode increases, and thus the quality of the device and the lifespan of the device may be decreased.

Here, in manufacturing the conductive polymer electrode, the conductive material should be uniformly dispersed in the solution. However, in dispersing the conductive material such as the nanotubes in the solution, the conductive material may be easily lumped due to the high cohesive force, and thus the resistance of the conductive polymer electrode is increased and the electric characteristics of the conductive polymer electrode is decreased.

Thus, the process for dispersing the conductive material in the solution uniformly should be developed.

Related prior arts are Korean laid-open patent No. 10-2012-0090594 and Korean laid-open patent No. 10-2016-0049555.

SUMMARY

The present invention is developed to solve the above-mentioned problems of the related arts. The present invention provides a method for manufacturing a conductive polymer electrode using a drop casting, in which the conductive polymer electrode is manufactured using a carbon nanofiber and polymer materials via a drop casting, so as to increase electric characteristics like electric conductivity.

According to an example embodiment, in the method for manufacturing a conductive polymer electrode, a conductive material is dispersed in a solution, to form a first mixing solution. A first polymer is added and dispersed to the first mixing solution, to form a second mixing solution. A second solution is added and dispersed to the second mixing solution, to form a third mixing solution. The third mixing solution is dropped on a hot plate using a pipette and a solution of the third mixing solution is evaporated, to form a conductive polymer. The adhesive patch is formed. The adhesive patch is attached to the conductive polymer.

In an example, the solution may include isopropyl alcohol (IPA), and the conductive material may include carbon nanofiber.

In an example, the first solution may include a monomer type solution of platinum-catalyzed silicones (EcoFlex™), and the second solution may include a cross-linking agent of platinum-catalyzed silicones (EcoFlex™).

In an example, in the forming the first mixing solution, the conductive material may be added to the solution, the conductive material may be dispersed in the solution using a vortex mixer, and the conductive material may be dispersed in the solution using a ultrasonic cleaner for a predetermined time.

In an example, in the forming the second mixing solution, the first solution may be added to the first mixing solution, the first solution may be dispersed in the first mixing solution using a vortex mixer, and the first solution may be uniformly dispersed in the first mixing solution using a ultrasonic cleaner for a predetermined time.

In an example, in the forming the third mixing solution, the second solution may be added to the second mixing solution, the second solution may be dispersed in the second mixing solution using a vortex mixer, and the second solution may be uniformly dispersed in the second mixing solution using a ultrasonic cleaner for a predetermined time.

In an example, an amount of each of the first solution and the second solution may be 1.5 times more than an amount of the conductive material.

In an example, the forming the conductive polymer may include pipetting the third mixing solution, to drop the third mixing solution to be coated on a petri dish, and heating the petri dish in the hot plate.

In an example, the pipetting the third mixing solution and the heating the petri dish may be repeated, to form the conductive polymer having a predetermined thickness.

In an example, the forming the adhesive patch may include coating Sylgard™ 184 solution on a wafer, and coating MG7-9850 solution on the wafer on which the Sylgard™ 184 solution is coated.

In an example, in the coating the Sylgard™ 184 solution on the wafer, Sylgard™ 184 monomer and Sylgard™ 184 crosslinking agent may be mixed with a ratio of 1:1, and a bubble generated in the mixing may be removed using a vacuum desiccator. The Sylgard™ 184 solution from which the bubble is removed may be spin-coated on the wafer, and the wafer may be hardened in the hot plate for a predetermined time.

In an example, in the coating the MG7-9850 on the wafer on which the Sylgard™ 184 solution is coated, MG7-9850 monomer and MG7-9850 crosslinking agent may be mixed with a ratio of 1:1, and a bubble generated in the mixing may be removed using a vacuum desiccator.

According to the present example embodiments, the mixing solution in which the conductive material and the polymer are mixed is dispersed using the drop casting and thus the solution is evaporated. Thus, the problem such as an increase of an electric resistance generated in the conventional dispersing in which the conductive material and the polymer are lumped may be effectively solved, and the polymer electrode having improved electric characteristics such as conductivity may be easily manufactured.

Here, to enhance the electric characteristics such as the conductivity, the number of the dropping of the mixing solution may be between 5 and 10, and the amount of each of the first solution which is a monomer and the second solution which is a crosslinking agent may be 1.5 times more than the amount of the conductive material, so that the polymer electrode having the enhanced conductivity may be easily manufactured.

Figure 1:
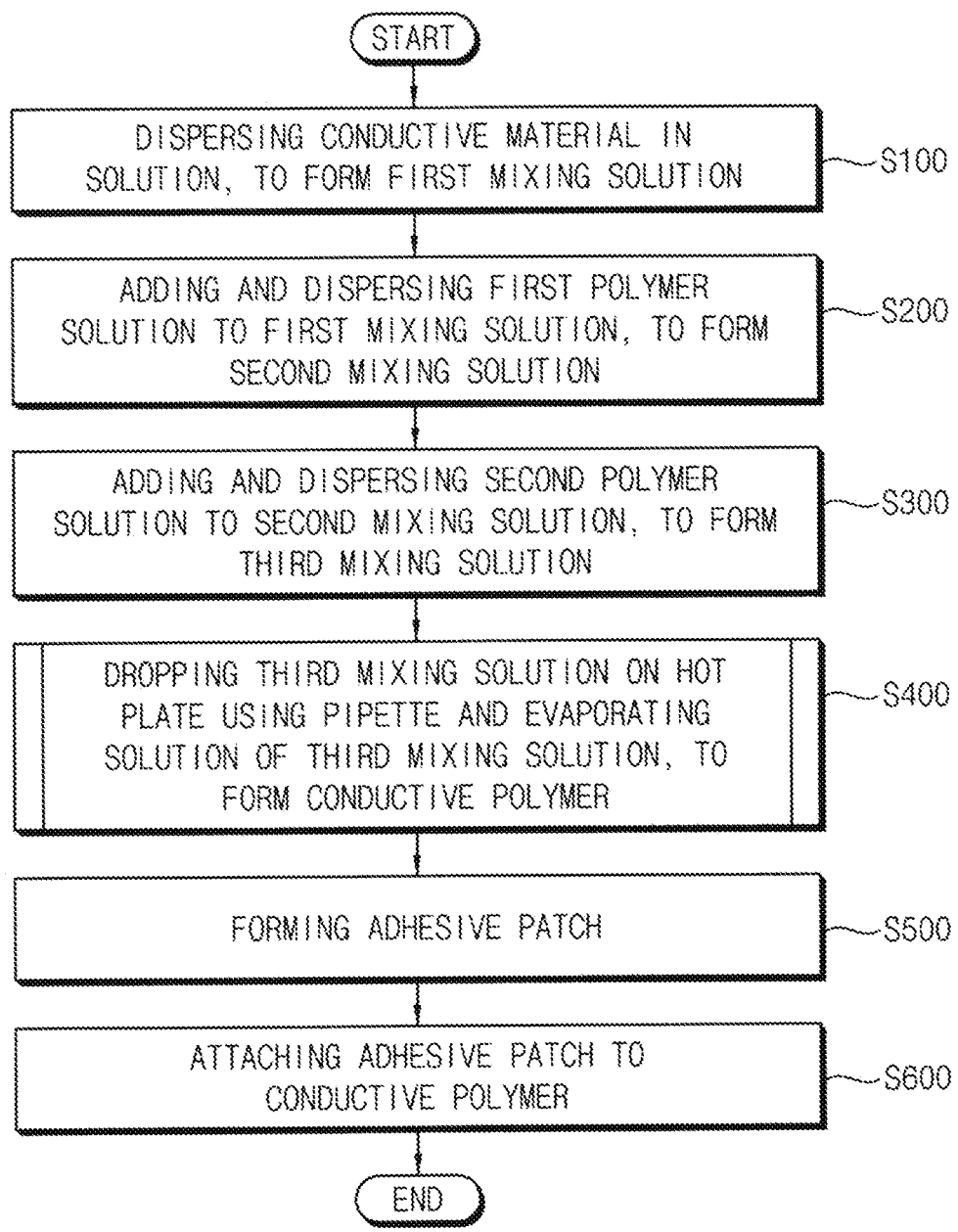
FIG. 1 is a flow chart showing a method for manufacturing a conductive polymer electrode using a drop casting according to an example embodiment of the present invention.

| * Reference numerals | |
|---|---|
| 20: conductive material | 30: first polymer solution |
| 40: second polymer solution | 50: conductive polymer |
| 100: first mixing solution | 200: second mixing solution |
| 300: third mixing solution | |

DETAILED DESCRIPTION

The invention is described more fully hereinafter with Reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. In the drawings, the size and relative sizes of layers and regions may be exaggerated for clarity.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention. Spatially relative terms, such as "beneath," "below," "lower," "above," "upper" and the like, may be used herein for ease of description to describe one element or feature's relationship to another element(s) or feature(s) as illustrated in the figures.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs.

It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The invention is described more fully hereinafter with reference to the accompanying drawings, in which embodiments of the invention are shown.

Figure 2:
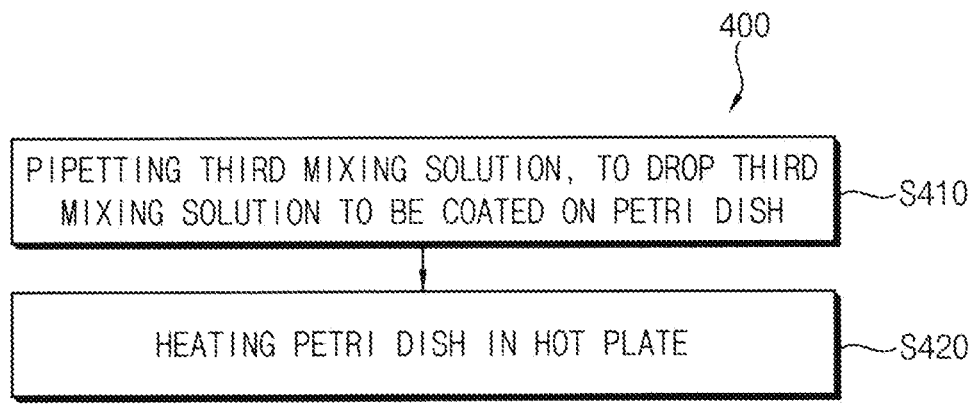
FIG. 2 is a flow chart showing a method for forming a conductive polymer in the method for manufacturing the conductive polymer electrode in FIG. 1; and FIG. 3A, FIG. 3B, FIG. 3C, FIG. 3D, FIG. 3E

FIG. 1 is a flow chart showing a method for manufacturing a conductive polymer electrode using a drop casting according to an example embodiment of the present invention. FIG. 2 is a flow chart showing a method for forming a conductive polymer in the method for manufacturing the conductive polymer electrode in FIG. 1. FIG. 3A, FIG. 3B, FIG. 3C, FIG. 3D, FIG. 3E and FIG. 3F shows process views illustrating a method for forming first, second and third mixing solutions and a method for forming the conductive polymer, in the method for manufacturing the conductive polymer electrode in FIG. 1.

Figure 3A:
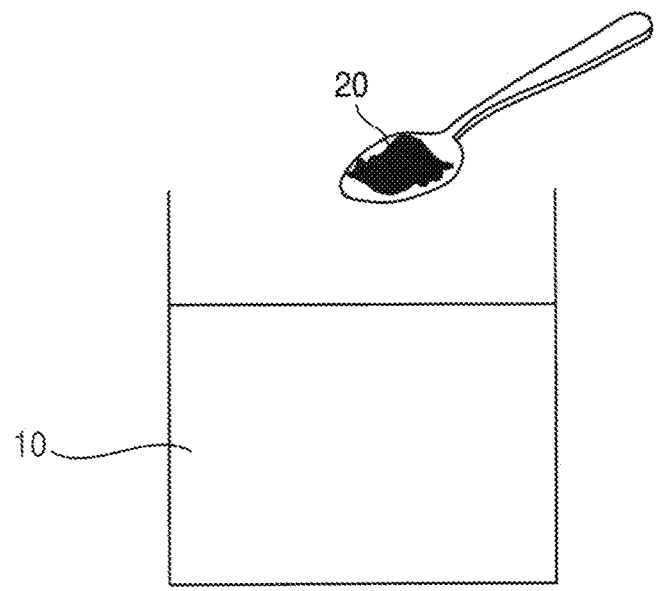
FIG. 3F shows process views illustrating a method for forming first, second and third mixing solutions and a method for forming the conductive polymer, in the method for manufacturing the conductive polymer electrode in FIG. 1.

Referring to FIG. 1 and FIG. 3A, in the method for manufacturing the conductive polymer electrode using the drop casting according to the present example embodiment, first, isopropyl alcohol (IPA) is used as a solution 10, and a conductive material 20 is dispersed in the solution 10, to form a first mixing solution 100 (step S100).

Here, the conductive material 20 may include carbon nanofiber.

For example, the conductive material 20 is added to the solution 10, and the conductive material 20 is entirely dispersed in the solution 10 using a vortex mixer. In addition, after the dispersion using the vortex mixer firstly, the conductive material 20 is additionally dispersed in the solution 10 using an ultrasonic cleaner, for about 100 minutes. Then, the conductive material 20 is uniformly dispersed in the solution 10, and the first mixing solution 100 is formed.

Here, as illustrated in FIG. 3A, a predetermined amount of the conductive material 20 is provided to the solution 10 at once and then is dispersed.

In addition, when the carbon nanofiber is used as the conductive material 20, the carbon nanofiber may include a nanostructure made of a circular shape graphene having a diameter between about 50 nm and about 200 nm. The above carbon nanofiber may have relatively high heat conductivity and high electric conductivity when mixed with a matrix material such as a plastic. Here, the carbon nanofiber may include a nanostructure having various kinds of shapes except for the circular shape.

Figure 3B:
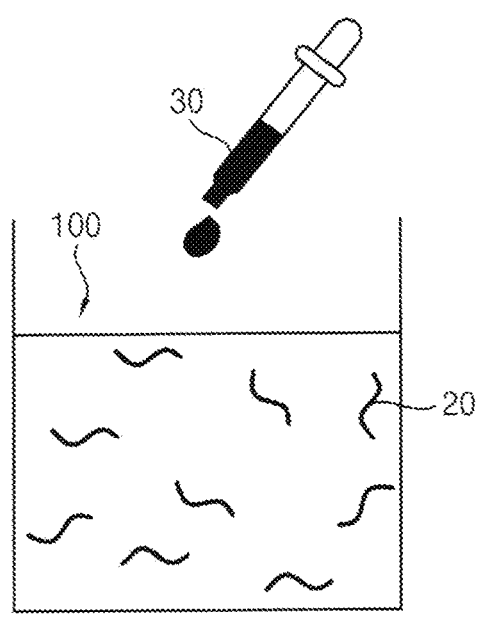

Then, referring to FIG. 1 and FIG. 3B, a first solution 30 is added to the first mixing solution 100 and the first solution 30 is dispersed in the first mixing solution 100, and then a second mixing solution 200 is formed (step S200).

For example, the first solution 30 is added to the first mixing solution 100, and the first solution 30 is entirely dispersed using the vortex mixer. In addition, after the dispersion using the vortex mixer firstly, the first solution 30 is additionally dispersed using the ultrasonic cleaner, for about 100 minutes. Then, the first solution 30 is uniformly dispersed in the first mixing solution 100, and the second mixing solution 200 is formed.

Here, as illustrated in FIG. 3B, a predetermined amount of the first solution 30 may be provided to the first mixing solution 100 at once, but alternatively, uniform amount of the first solution 30 may be provided to the first mixing solution 100 repeatedly with the same amount and with the same interval.

For example, the first solution 30 may include EcoFlex™ 0030 manufactured by Smooth-On Inc., and in the present example embodiment, the first solution 30 may be a monomer type solution.

Figure 3C:
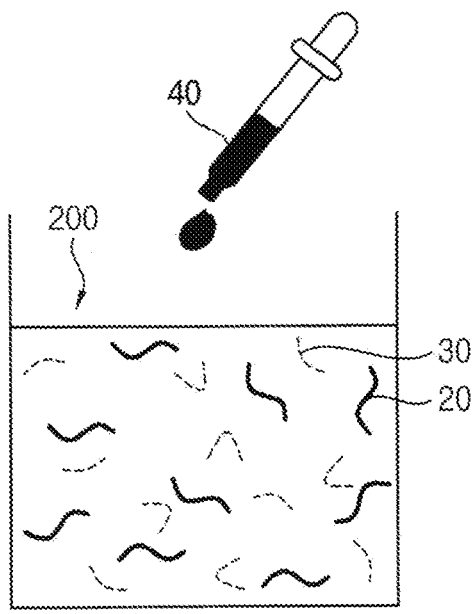

Then, referring to FIG. 1 and FIG. 3C, a second solution 40 is added to the second mixing solution 200, and the second solution 40 is dispersed in the second mixing solution 200, to form a third mixing solution 300 (step S300).

For example, the second solution 40 is added to the second mixing solution 200, and the second solution 40 is entirely dispersed using the vortex mixer. In addition, after the dispersion using the vortex mixer firstly, the second solution 40 is additionally dispersed using the ultrasonic cleaner, for about 100 minutes. Then, the second solution 40 is uniformly dispersed in the second mixing solution 200, and the third mixing solution 300 is formed.

Here, as illustrated in FIG. 3C, a predetermined amount of the second solution 40 may be provided to the second mixing solution 200 at once, but alternatively, uniform amount of the second solution 40 may be provided to the second mixing solution 200 repeatedly with the same amount and with the same interval.

For example, the second solution 40 may include Eco-Flex™ 0030 manufactured by Smooth-On Inc., and in the present example embodiment, the second solution 40 may be a cross-linking agent.

Figure 3D:
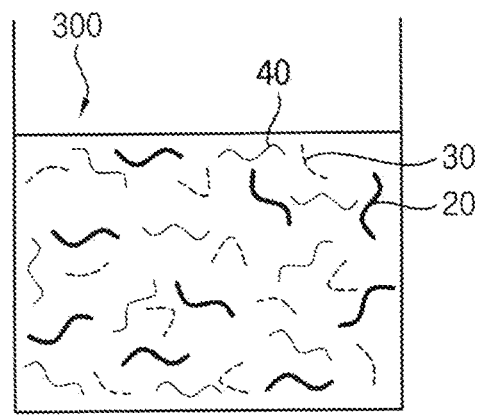
Figure 3E:
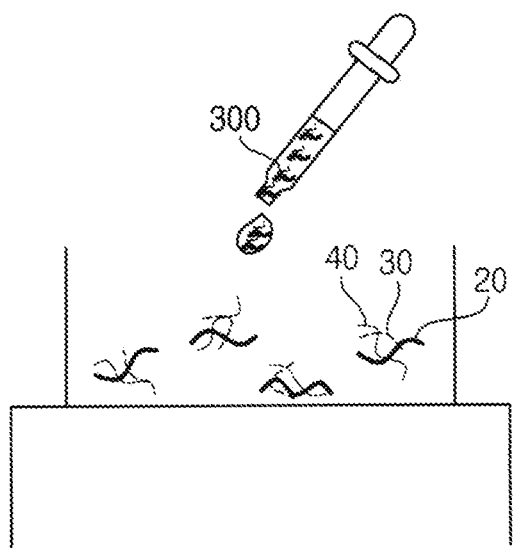

Then, as illustrated in FIG. 3D, the third mixing solution 300 in which the conductive material 20, the first solution 30 and the second solution 40 are mixed in the solution 10 is completely manufactured. Then, referring to FIG. 1 and FIG. 3E, the third mixing solution 300 is dropped on a hot plate using a pipette, which is the drop casting, and thus the solution 10 included in the third mixing solution 300, which is the isopropyl alcohol, is evaporated. Then, a conductive polymer is formed (step S400).

Here, in forming the conductive polymer, as illustrated in FIG. 2, firstly, a predetermined amount of third mixing solution 300 is pipetted to be dropped, and thus the third mixing solution 300 is coated on a petri dish (step S410). Then, the petri dish is positioned on a hot plate and is heated for a predetermined time (step S420).

For example, 1 mL of third mixing solution 300 may be pipetted. The petri dish on which the third mixing solution 300 is coated may be heated on the hot plate with a temperature of about 75° C. for about 30 minutes.

Figure 3F:

The steps (step S410 and step S420) are repeated at least five times, and then the conductive polymer 50 having a predetermined thickness may be manufactured, as illustrated in FIG. 3F.

In the present example embodiment, in pipetting the third mixing solution 300 and dropping the third mixing solution 300 on the petri dish, the drop casting is applied so that the third mixing solution 300 may be coated on the petri dish with a constant thickness. Thus, after the solution included the dropped third mixing solution 300 is entirely evaporated as the dropped third mixing solution 300 is heated on the hot plate, the third mixing solution 300 may be additionally dropped on the petri dish to be coated on the petri dish by a predetermined thickness, and then the heating and the evaporating may be repeated.

Accordingly, after the solution 10 included in the third mixing solution 300 is evaporated from the petri dish on which the third mixing solution 300 is coated with a uniform thickness, the third mixing solution 300 is dropped and coated on the petri dish again and the evaporating and the dropping are repeated, until the conductive polymer 50 having the predetermined thickness is manufactured.

Here, using the drop casting, the conductive polymer having the predetermined thickness is coated and formed repeatedly. Thus, the problem caused in the conventional manufacturing method for the conductive polymer may be solved. That is, in the conventional manufacture method, the heat is provided to relatively large amount of mixing solution at once in the evaporating step without coating the mixing solution on the petri dish by a relatively thin thickness, and thus in the evaporating step, the conductive materials and so on included in the mixing solution are lumped, so that the resistance of the conductive polymer may be increased to decrease the electric characteristics of the conductive polymer.

Further, in addition to manufacturing the conductive polymer, an adhesive patch is formed to manufacture the conductive polymer electrode (step S500).

In forming the adhesive patch, Sylgard™ 184 solution is coated on a wafer, and then MG7-9850 solution is coated on the wafer on which the Sylgard™ 184 solution is coated.

For example, for coating the Sylgard™ 184 solution on the wafer, Sylgard™ 184 monomer and Sylgard™ 184 crosslinking agent are mixed with a ratio of 1:1, and a bubble generated in the mixing is removed using a vacuum desiccator. In addition, the Sylgard™ 184 solution from which the bubble is removed is spin-coated with the number of revolutions between about 200 rpm and about 500 rpm on the wafer using a spin-coater, and the wafer is hardened in the hot plate with a temperature of about 120° C. for a predetermined time.

Then, for coating the MG7-9850 solution on the wafer on which the Sylgard™ 184 solution is coated, MG7-9850 monomer and MG7-9850 crosslinking agent are mixed with a ratio of 1:1, and a bubble generated in the mixing is removed using the vacuum desiccator. In addition, the MG7-9850 solution from which the bubble is removed is spin-coated with the number of revolutions between about 200 rpm and about 500 rpm on the wafer using the spin-coater, and the wafer is hardened in the hot plate with a temperature of about 120° C. for a predetermined time.

Thus, the adhesive patch is formed.

Then, the adhesive patch is attached to the conductive polymer 50 (step S600).

Here, the conductive polymer is cut to be fitted to a size of the adhesive patch, for the adhesive patch to cover an entire surface of the conductive polymer 50. Thus, the adhesive patch entirely covers the conductive polymer and is to be stably attached on a skin.

Table 1 shows a change of a resistance of the third mixing solution according to the number of drops of the third mixing solution in which the conductive material CNF, the first solution EcoFlex™ A and the second solution Eco-Flex™ B.

TABLE 1

| Change of resistance according to number of drops | | | |
|---|---|---|---|
| IPA [g] | CNF [g] | ECOFLEX 0030 A [g] | ECOFLEX 0030 B [g] |
| 60 | 1 | 1.75 | 1.75 |

| Number of drops | 5 times | 10 times | 15 times | 20 times |
|---|---|---|---|---|
| Resistance [kΩ] | 20 | 9 | 31 | 29 |
| | 14 | 5 | 54 | 30 |
| | 17 | 7 | 40 | 33 |
| | 24 | 8 | 50 | 54 |
| Mean value | 18.75 | 7.25 | 43.75 | 36.5 |

Referring to Table 1, the resistance is relatively large in the cases in which the number of the drops is 15 times and 20 times, and the resistance is relatively large in the case in which the number of the drops is 5 times. However, the resistance is relatively small in the case in which the number of the drops is 10 times. Thus, the electric characteristics may be great at the case in which the number of the drops is 10 times.

Table 2 shows a change of the resistance of the third mixing solution according to a change of the amount of each of the conductive material CNF, the first solution EcoFlex™ A and the second solution EcoFlex™ B, with the constant amount of the solution which is isopropyl alcohol (IPA).

TABLE 2

Change of resistance according to change of CNF, ecoflex A and ecoflex B

| Examples | 1 | 2 | 3 | 4 | 5 | 6 |
|---|---|---|---|---|---|---|
| IPA [g] | 30 | 30 | 30 | 30 | 30 | 30 |
| CNF [g] | 0.5 | 0.5 | 0.5 | 1 | 1 | 1 |
| ECOFLEX A [g] | 1 | 0.75 | 0.5 | 2 | 1.5 | 1 |
| ECOFLEX B [g] | 1 | 0.75 | 0.5 | 2 | 1.5 | 1 |
| Resistance [kΩ] | 109 | 7 | 5 | 129 | 9 | 22 |
|  | 120 | 7 | 6 | 106 | 9 | 20 |
|  | 194 | 5 | 22 | 132 | 7 | 17 |
|  | 164 | 5 | 18 | 74 | 10 | 11 |
| Mean value [kΩ] | 147 | 6 | 13 | 110 | 9 | 17.5 |

Referring to Table 2, the amount of the isopropyl alcohol is fixed with 30 g and the amount of the conductive material is changed with 0.5 g and 1 g, and thus the ratio between the solution and the conductive material is changed. In addition, the amount of each of the first and second solutions is changed with 1 time, 1.5 times and 2 times larger than that of the conductive material.

Thus, as shown in Example 2 and Example 5, when the amount of each of the first and second solutions is 1.5 times larger than the amount of the conductive material, the electric characteristics are the best, compared to other examples.

According to the present example embodiments, the mixing solution in which the conductive material and the polymer are mixed is dispersed using the drop casting and thus the solution is evaporated. Thus, the problem such as an increase of an electric resistance generated in the conventional dispersing in which the conductive material and the polymer are lumped may be effectively solved, and the polymer electrode having improved electric characteristics such as conductivity may be easily manufactured.

Here, to enhance the electric characteristics such as the conductivity, the number of the dropping of the mixing solution may be between 5 and 10, and the amount of each of the first solution which is a monomer and the second solution which is a crosslinking agent may be 1.5 more than the amount of the conductive material, so that the polymer electrode having the enhanced conductivity may be easily manufactured.

Although the exemplary embodiments of the present invention have been described, it is understood that the present invention should not be limited to these exemplary embodiments but various changes and modifications can be made by one ordinary skilled in the art within the spirit and scope of the present invention as hereinafter claimed.

What is claimed is:

1. A method for manufacturing a conductive polymer electrode, the method comprising:
    dispersing a conductive material of carbon nanofiber in a solution of isopropyl alcohol (IPA), to form a first mixing solution;
    adding and dispersing a first solution to the first mixing solution, to form a second mixing solution;
    wherein the first solution includes a monomer type solution of platinum catalyzed silicones (EcoFlex™),
    adding and dispersing a second solution to the second mixing solution, to form a third mixing solution;
    wherein the second polymer solution includes a crosslinking agent of platinum catalyzed silicones (EcoFlex™),
    dropping the third mixing solution on a substrate on a hot plate using a pipette and evaporating a solution of the third mixing solution, to form a conductive polymer;
    forming an adhesive patch; and
    attaching the adhesive patch to the conductive polymer,
    wherein a weight of each of the first solution and the second solution is 1.5 times more than a weight of the conductive material;
    wherein in the forming the first mixing solution, adding the conductive material to the solution, dispersing the conductive material in the solution using a vortex mixer, and dispersing the conductive material in the solution using a ultrasonic cleaner for a predetermined time;
    wherein in the forming the second mixing solution, adding the first solution to the first mixing solution, dispersing the first solution in the first mixing solution using a vortex mixer, and uniformly dispersing the first solution in the first mixing solution using a ultrasonic cleaner for a predetermined time; and,
    wherein in the forming the third mixing solution, adding the second solution to the second mixing solution, dispersing the second solution in the second mixing solution using a vortex mixer, and uniformly dispersing the second solution in the second mixing solution using a ultrasonic cleaner for a predetermined time.

2. The method of claim 1, wherein the pipetting the third mixing solution and the heating the substrate are repeated, to form the conductive polymer having a predetermined thickness.

* * * * *